United States Patent
Leet et al.

[11] Patent Number: 6,036,658
[45] Date of Patent: Mar. 14, 2000

[54] CERVICAL TISSUE SAMPLING DEVICE AND METHOD

[76] Inventors: Richard A. Leet, 3118 Williamsburg, NW., Warren, Ohio 44485; Deborah L. Rowlands, 2697 Oak Forest Dr., Niles, Ohio 44446

[21] Appl. No.: 09/087,991

[22] Filed: Jun. 1, 1998

Related U.S. Application Data

[63] Continuation-in-part of application No. 08/891,257, Jul. 10, 1997, Pat. No. 5,795,309.

[51] Int. Cl.[7] ........................................ A61B 5/00
[52] U.S. Cl. ............................................. 600/569
[58] Field of Search ........................ 600/562, 569–572; 206/569–571

[56] References Cited

U.S. PATENT DOCUMENTS

| | | | |
|---|---|---|---|
| 2,739,585 | 3/1956 | Ayre | 600/569 |
| 3,626,470 | 12/1971 | Antonides | 600/572 |
| 3,890,954 | 6/1975 | Greenspan . | |
| 4,324,262 | 4/1982 | Hall | 128/756 |
| 4,653,510 | 3/1987 | Koll | 600/569 |
| 5,339,828 | 8/1994 | Keating et al. . | |
| 5,456,265 | 10/1995 | Yim | 600/569 |
| 5,462,063 | 10/1995 | Kist et al. | 600/569 |

*Primary Examiner*—Max Hindenburg
*Attorney, Agent, or Firm*—Harpman & Harpman

[57] ABSTRACT

A self-actuated sampling instrument for the collection and short term preservation of cervical tissues for testing purposes by remote laboratory. The sampling and preserving device includes a collection cylinder and a retractable plunger having a sampling broom thereon. A containment collection chamber within the collection cylinder providing a sterile transportation container for the tissue sample which is suspended in a preservative gel that is mechanically disposed from within the collection cylinder onto the sampling broom by the user before transportation to the laboratory.

10 Claims, 4 Drawing Sheets

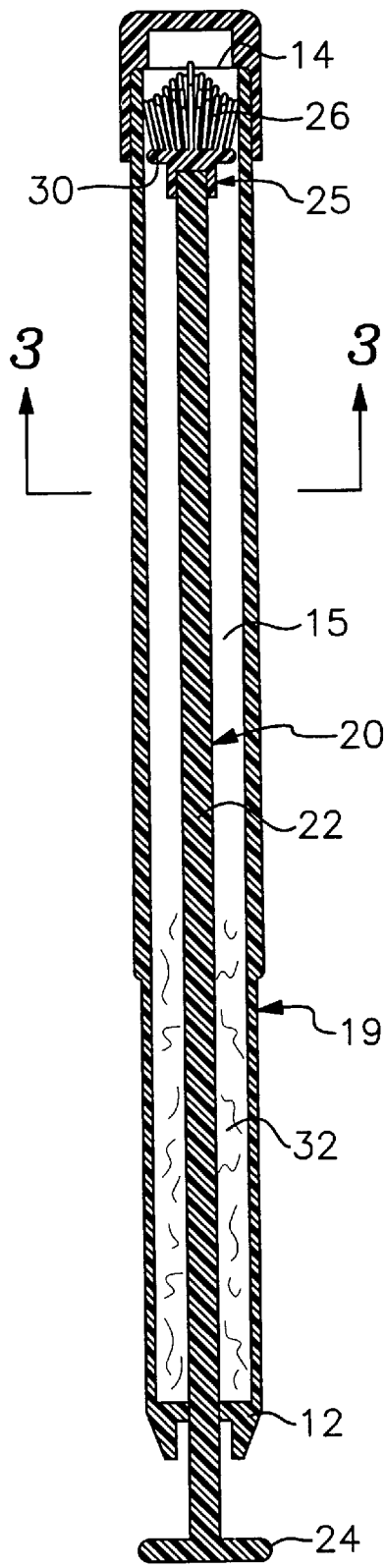
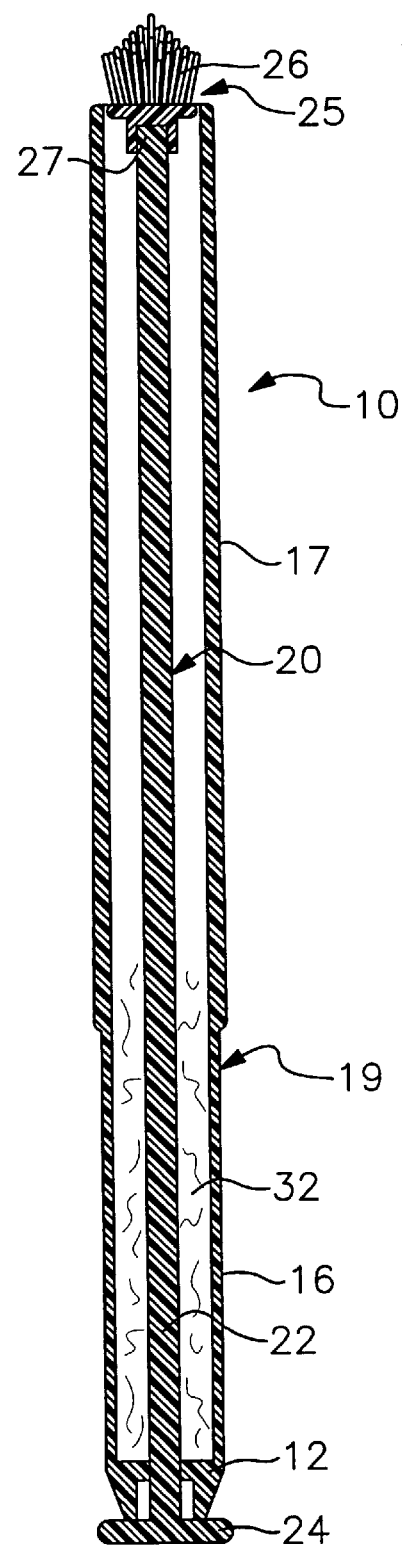
Fig. 1
Fig. 2

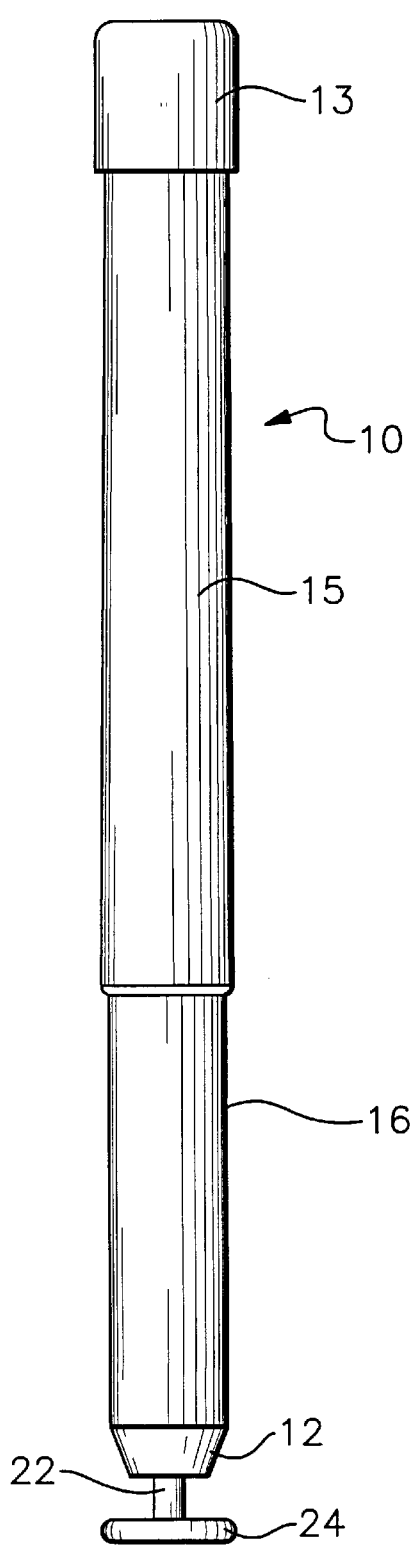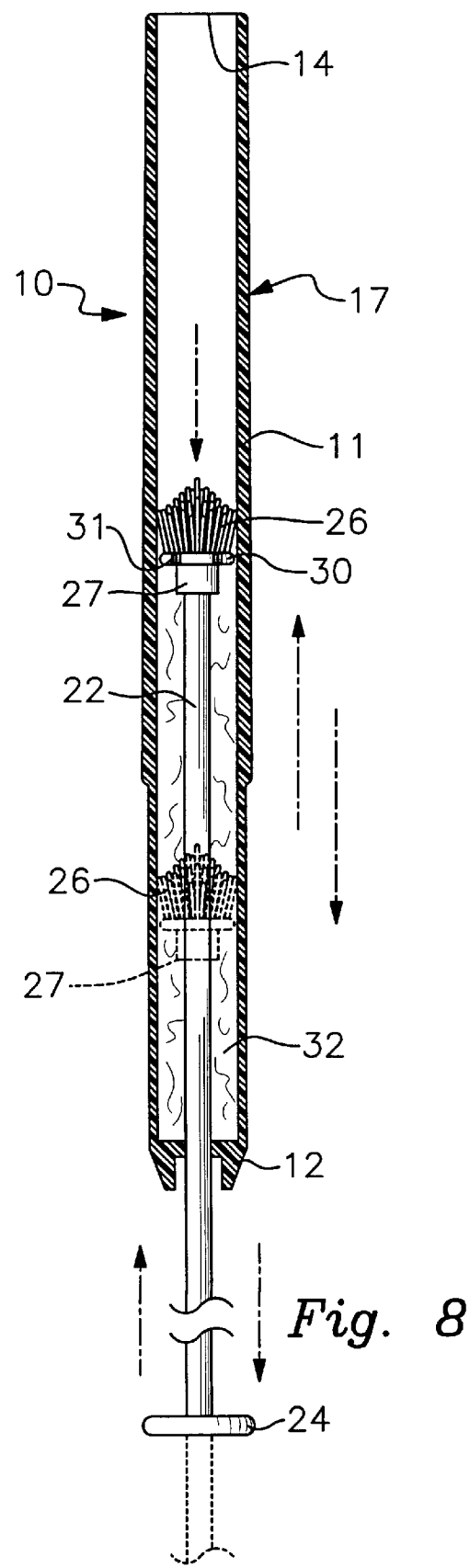
Fig. 7
Fig. 8

CERVICAL TISSUE SAMPLING DEVICE AND METHOD

This is a CIP patent application of Ser. No. 08/891,257, filed Jul. 10, 1997, now U.S. Pat. No. 5,795,309.

BACKGROUND OF THE INVENTION

1. Technical Field

This device relates to collection apparatus for cervical tissue sampling by women at home and the transportation of the samples to an offsite testing facility.

2. Description of Prior Art

Prior art devices of this type have been developed to sample and transport cervical tissue for testing by using insertion elements with attached sampling media surfaces, see for examples U.S. Pat. Nos. 3,890,954, 4,324,262, and 5,339,828.

In U.S. Pat. No. 3,890,954 is a method and apparatus for collecting cultures with a swab in a tube containing a culture sustaining liquid in one end with a one way isolation valve above the liquid. As the swab is advanced the valve allows transfer of the liquid to the swab, and U.S. Pat. No. 4,324,262 discloses an aspirating culture catheter and method of use in which a catheter is used to transport a sampling device within the body of a human having an inner tube with a swab extensible out through a balloon type sealing element.

U.S. Pat. No. 5,339,828 is directed to an apparatus and method for taking cultures endoscopically having a sampling swab on an elongated extension within the transfer body.

SUMMARY OF THE INVENTION

A self-contained sampling and transportation device for the collection of cervical samples. The device retrieves and then preserves the sample within its retrieving structure by suspending the sample in a preservative gel which is contained within the sampling device. An interlocking containment enclosure assures one-time use and secure seal of the specimen within the collection device for transportation via mail or other means to an offsite testing laboratory.

DESCRIPTION OF THE DRAWINGS

FIG. 1 is a cross-sectional view of the sampling and transportation device in pre-use position;

FIG. 2 is cross-sectional view of the sampling transportation device in open extended sample position;

FIG. 7 is a side elevational view of the sampling and transportation device of the invention in closed transport position;

FIG. 8 is a cross-sectional view of the sampling and transportation device in use wherein a sample has been collected.

DESCRIPTION OF THE PREFERRED EMBODIMENT

Figure 3:
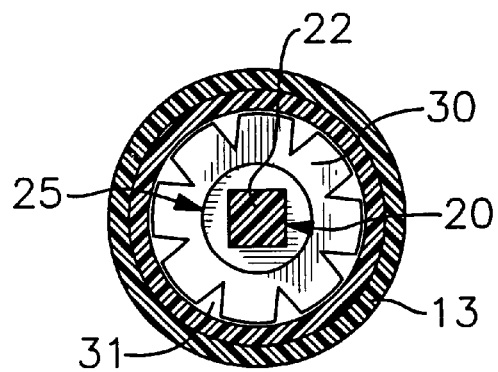
FIG. 3 is an enlarged cross-section on lines 3—3 of FIG. 1.

Referring to FIGS. 1, 3 and 7 of the drawings, a cervical self-contained sampling and transportation device of the invention can be seen including an elongated rigid collection cylinder 11 having a tapered apertured annular end fitting 12 and an oppositely disposed end cap 13 frictionally engaged over the open end at 14 thereof. The collection cylinder 11 defines a collection and preserving chamber 15 therein.

The outer surface of the collection cylinder 11 has a handle portion 16 and an insertion portion 17 with the handle portion 16 having a smaller outside diameter than that of the insertion portion and is defined by a transition point 19 as will be understood by those skilled in the art and as best seen in FIG. 7 of the drawings.

A sampling plunger 20 extends from within the collection cylinder 11 through an access area opening at 21 in the tapered annular end fitting 12 as hereinbefore described. The plunger 20 has a cross-sectionally square shaft 22 that is engaged through a registration openings at 23 which forms a seal about the shaft 22 within the recess 21 in the tapered apertured annular end fitting 12. The free end of the shaft 20 that extends from the collection cylinder 11 has an activation knob 24 on its distal end. A collection fitting 25 is removably secured to the shaft's free end with a compound collection broom 26 formed thereon as best seen in FIGS. 1, 4, 5 and 6 of the drawings.

Figure 5:
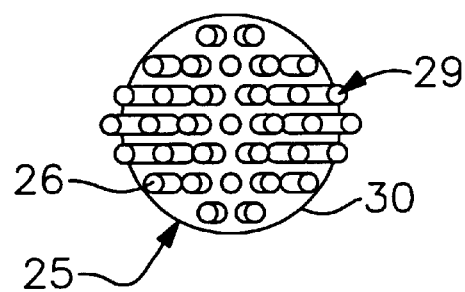
FIG. 5 is an enlarged top plan view of the sampling broom shown in FIG. 4.
Figure 4:
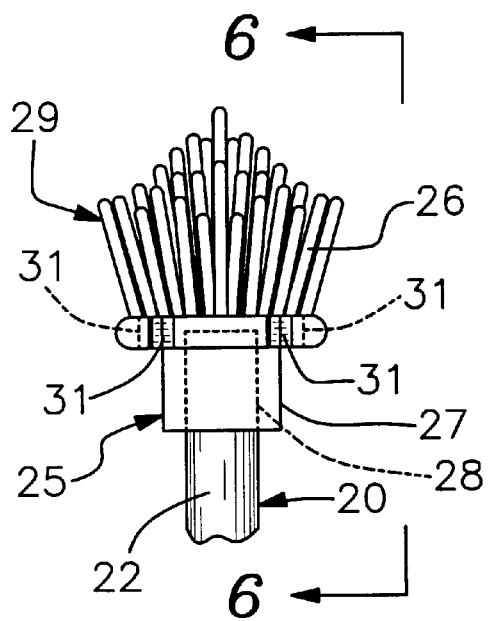
FIG. 4 is an enlarged side elevational view of the sample broom of the invention.
Figure 6:
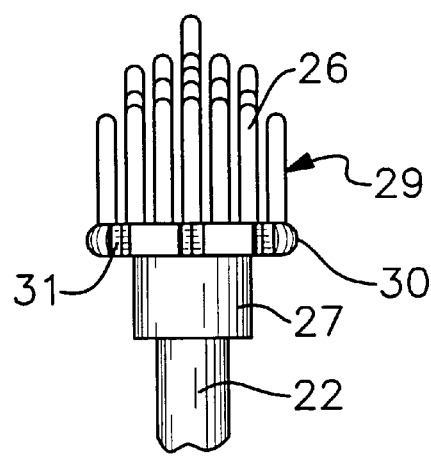
FIG. 6 is an enlarged side elevational view of the sampling broom on lines 6—6 of FIG. 4.

The collection fitting 25 has a shaft engagement base 27 with a registering recess 28 therein, best seen in FIGS. 4 and 6 of the drawings. The collection broom 26 is formed of a plurality of synthetic resin bristles 29 of varying lengths that extend from a bristle support disk 30 in longitudinal spaced multiple rows 30A as best seen in FIGS. 5 and 6 of the drawings. The bristles 29 are angularly disposed (off) vertical in their respective longitudinal rows as clearly seen in FIGS. 4 and 5 of the drawings, thus increasing the overall width in the horizontal plane as seen in FIG. 4. The bristles "offset" as hereinbefore described increases the exposed collection surface of the bristles 29 improving the sampling gathering efficiency and to help conform to the natural shape of the human cervix (not shown) onto which they are to be engaged to provide segmented bristle engagement for maximized sampling of the surface.

The bristle support disk 30 is of a registering diameter within the collection cylinder 11 and has a plurality of annular spaced notches 31 extending inwardly from its perimeter edge as best seen in FIG. 3 of the drawings.

Referring back now to FIGS. 1 and 2 of the drawings, it will be seen that the collection cylinder 11's thin wall cylinder body shape having the plunger 20 positioned within and that the end cap closure 13 is secured thereon defining a sealed environment within. The collection chamber 15, hereinbefore described, is partially filled with a specimen preserving gel 32 which is available commercially for preserving human cell specimens for transportation and later laboratory analysis as is understood in the prior art.

The specimen preserving gel 32 is typically positioned within the "handle portion 16" of the collection chamber 15, but is not restricted to that location in that the only requirement is that the gel must be opposite the bristles 26 before use.

In use, the sample and transportation device 10 of the invention is shipped to the end user as seen in FIG. 1 of the drawings with the activation knob 24 not fully engaged against the end fitting 12. The end cap 13 is then removed by the "user" (not shown) and the device 10 is inserted by the user. After insertion, the plunger 20 is pushed inwardly advancing the attached collection broom 26 outwardly from the opening 14 of the collection cylinder 11 as illustrated in FIG. 2 of the drawings.

The female user then rotates the collection cylinder 11 with the integrally attached collection broom 26 via the handle portion 16 retrieving a tissue sample (not shown) thereon for testing purposes.

Figure 9:
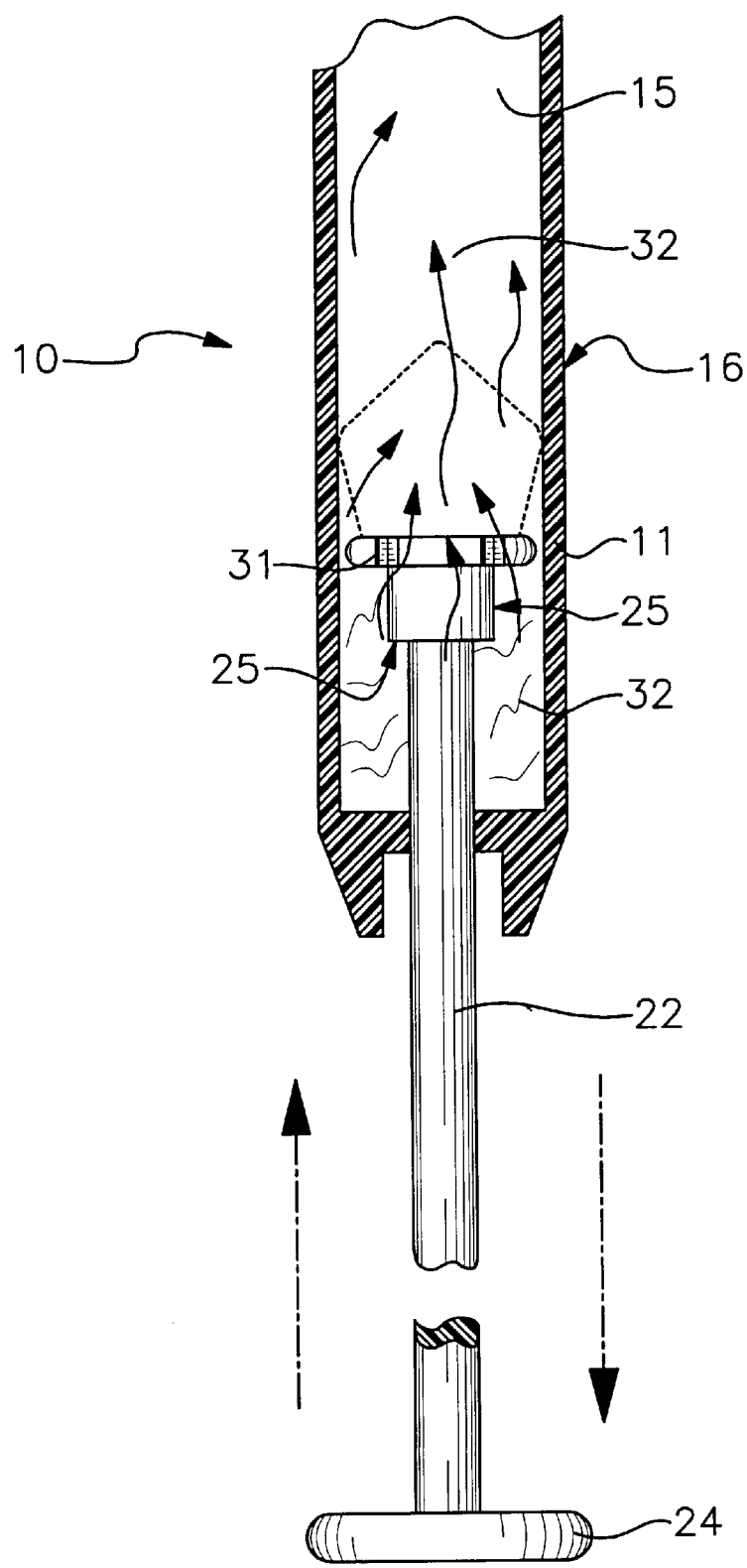
FIG. 9 is an enlarged partial cross-sectional view of the collection broom shown in broken lines in full engagement surrounded by the preservative gel after sample is retrieved.

The device is then withdrawn from the female user and the plunger 20 is pulled outwardly via the knob 24 retracting the sampling broom 26 within the collection cylinder 11. The end cap 13 is then repositioned on the open end 14 sealing the collection cylinder re-establishing the collection chamber 15 as hereinbefore described. After confirmation that the collection cylinder 11 is sealed, the plunger 20 is continued to be pulled outwardly via the knob 24 which draws the sample broom 26 back through the collection cylinder 11 engaging the preserving gel 32 as best seen in FIGS. 8 and 9 of the drawings. As the broom 26 is advanced, the specimen preserving gel 32 is forced through the notches 31 around the support disk 30 and onto the collection bristles 29. To assure proper specimens coating with the specimens preserving gel, the broom 29 is drawn down fully against the tapered apertured annular end fitting 12. Repeated plunger oscillation will assure that the specimen is immersed within the preserving gel. The plunger is then pushed back into the collection cylinder 11 advancing the broom 26 within the end cap 13 signifying that the sampling and transportation device of the invention is ready for shipping to a remote location as seen in FIG. 7 of the drawings. The sampling device of the invention is shipped via U.S. mail or other means to an offsite laboratory for testing.

It will be evident to those skilled in the art that various changes and modifications may be made therein without departing from the spirit of the invention.

Therefore I claim:

1. A cervical tissue sampling and transportation device comprising; a collection cylinder, a plunger disposed for reciprocally sliding movement within said cylinder, a collection chamber within said collection cylinder, a collection broom secured to the distal end of said plunger, said collection broom having a plurality of resilient bristles extending from a support disk having a plurality of annularly spaced notches extending inwardly from a perimeter edge thereof, a closure removably positioned in sealing relation over an open end portion of said collection cylinder, means for transferring contents of said collection chamber to said collection broom.

2. The cervical testing sampling and transportation device of claim 1 wherein said resilient bristles define a convex engagement end surface.

3. The cervical tissue sampling and transportation device of claim 1 wherein said collection chamber contains a preserving gel.

4. The cervical tissue sampling and transportation device of claim 1 wherein said collection cylinder has an area of increased diameter and an apertured end fitting through which said plunger extends.

5. The cervical tissue sampling and transportation device of claim 1 wherein a portion of said plunger extends from said collection cylinder has an activation knob of a diameter equal to that of said known diameter of said collection chamber.

6. The cervical tissue sampling and transportation device of claim 1 wherein said means for transferring contents of said collection chamber to said collection broom comprises a broom mounting assembly on said plunger in said collection cylinder wherein said broom mounting assembly has a shaft, engagement base with said support disk thereon.

7. A cervical tissue sampling and transportation device comprising a collection cylinder of a known length, a plunger disposed for reciprocally sliding movement within said collection cylinder, said plunger of a length equal to that of said known length of said collection cylinder, a collection broom secured to the distal end of said plunger within said collection cylinder, a collection chamber within a portion of said collection cylinder, specimen preserving gel within said collection chamber, said collection broom movable from a first position within a portion of said collection cylinder to a second position outside said collection cylinder, to a third position within said collection chamber, to a fourth position in a sealing end cap positioned over the open end of said collection cylinder, a broom mounting disk having a plurality of notches extending inwardly from its perimeter edges.

8. The cervical tissue sampling and transportation device of claim 7, wherein said collection broom comprises a set of resilient bristles extending from said broom mounting disk defining a convex surface.

9. The cervical tissue sampling and transportation device of claim 8, wherein said bristle sets are of varying vertical dimension and are angularly disposed in relation to one another.

10. The cervical tissue sampling and transportation device of claim 9, wherein said bristles are formed of synthetic resin material.

* * * * *